United States Patent [19]

Wertheimer

[11] 4,265,538

[45] May 5, 1981

[54] OPTICAL SAMPLE CELL FOR ANALYSIS OF PARTICLES IN LIQUID SUSPENSION

[75] Inventor: Alan L. Wertheimer, North Wales, Pa.

[73] Assignee: Leeds & Northrup Company, North Wales, Pa.

[21] Appl. No.: 86,227

[22] Filed: Oct. 18, 1979

[51] Int. Cl.³ .................. G01N 21/05; G01N 15/02
[52] U.S. Cl. .................. 356/246; 356/336; 356/343; 250/576
[58] Field of Search .............. 356/246, 336, 339, 343; 250/574, 575, 576

[56] References Cited

U.S. PATENT DOCUMENTS

| 3,873,206 | 3/1975 | Wilcock | 356/338 |
| 4,134,679 | 1/1979 | Wertheimer | 356/336 |

OTHER PUBLICATIONS

"The Optical Measurement of Aerosols"; Aerosol Science, edited by C. N. Davis, Academic Press; London 1966.

*Primary Examiner*—Vincent P. McGraw
*Attorney, Agent, or Firm*—William G. Miller, Jr.; Raymond F. MacKay

[57] ABSTRACT

A rectangular sample cell for use in the measurement of the light scattered from an incident light beam in three mutually orthogonal directions is constructed with a prism having its base optically in contact with the sample along a side of the cell. Two other faces of the prism are oriented at equal angles to the base so that those faces pass orthogonal components of the light scattered at 90° from the axis of the incident beam. The other orthogonal component is formed by the forward scattered light.

8 Claims, 8 Drawing Figures

OPTICAL SAMPLE CELL FOR ANALYSIS OF PARTICLES IN LIQUID SUSPENSION

BACKGROUND OF THE INVENTION

This invention relates to sample cells designed to receive for optical analysis a flowing sample of liquid suspended particles. When it is desired to measure the total volume of the particles in the sample or their volume distribution, it is necessary to use two analytical systems when the particle sizes range widely as from 0.1 microns to a size beyond 10 microns. It is known, for example, that the use of an analytical system such as that disclosed in U.S. Pat. No. 3,873,206 issued to William Leslie Wilcock on Mar. 25, 1975 can be utilized to measure the volume of particles in the range of 2.0 to 100 microns by measuring the forward scattered light produced by a light beam incident to the sample when an appropriate spatial filter is used. It is also known that the analytical system of U.S. Pat. No. 4,134,679 issued to the present inventor on Jan. 16, 1979 can be utilized to measure the volume of particles in the range of 0.1 to 10 microns in diameter by measuring the light scattered by the particles at 90° from the axis of an incident beam whose wavelength is twice the diameter of the particles being measured when the measurement uses two orthogonal polarizations. U.S. Pat. Nos. 3,873,206 and 4,134,679 are hereby incorporated by reference as a part of this specification.

In order to efficiently use the two above mentioned analytical systems to measure particle volume in the range of 0.1 to 100 microns without the necessity of using two separate instruments with the inevitable difficulties involved in coordinating the results and avoiding expensive duplication, it is necessary to make the two measurements, that is the forward scattering and the 90° scattering measurements at the same time, or in a short time span making any necessary computations later.

It is therefore an object of this invention to provide a sample cell whose structure will make possible the measurement of the forward scattered light and the 90° scatter in two orthogonal directions without the introduction of wells, insertions, or bends in the sample stream which can create turbulence.

SUMMARY OF THE INVENTION

This invention provides a straight path sample cell for optically analyzing the light scattered by particles suspended in a flowing liquid sample by measuring the components of light scattered in three mutually orthogonal directions from an incident light beam directed in one of those directions and polarized in another. The cell structure has an entrance and an exit window which respectively form a front and back for the cell so that the incident light beam is received by the front and the forward scattered light is transmitted through the back as one of the components. The cell also has a prism means with at least one of its faces optically contacting the sample along a side of the cell. Two other faces of the prism means are oriented so that they each pass another component of the scattered light.

DESCRIPTION OF THE PREFERRED EMBODIMENTS

Figure 1:
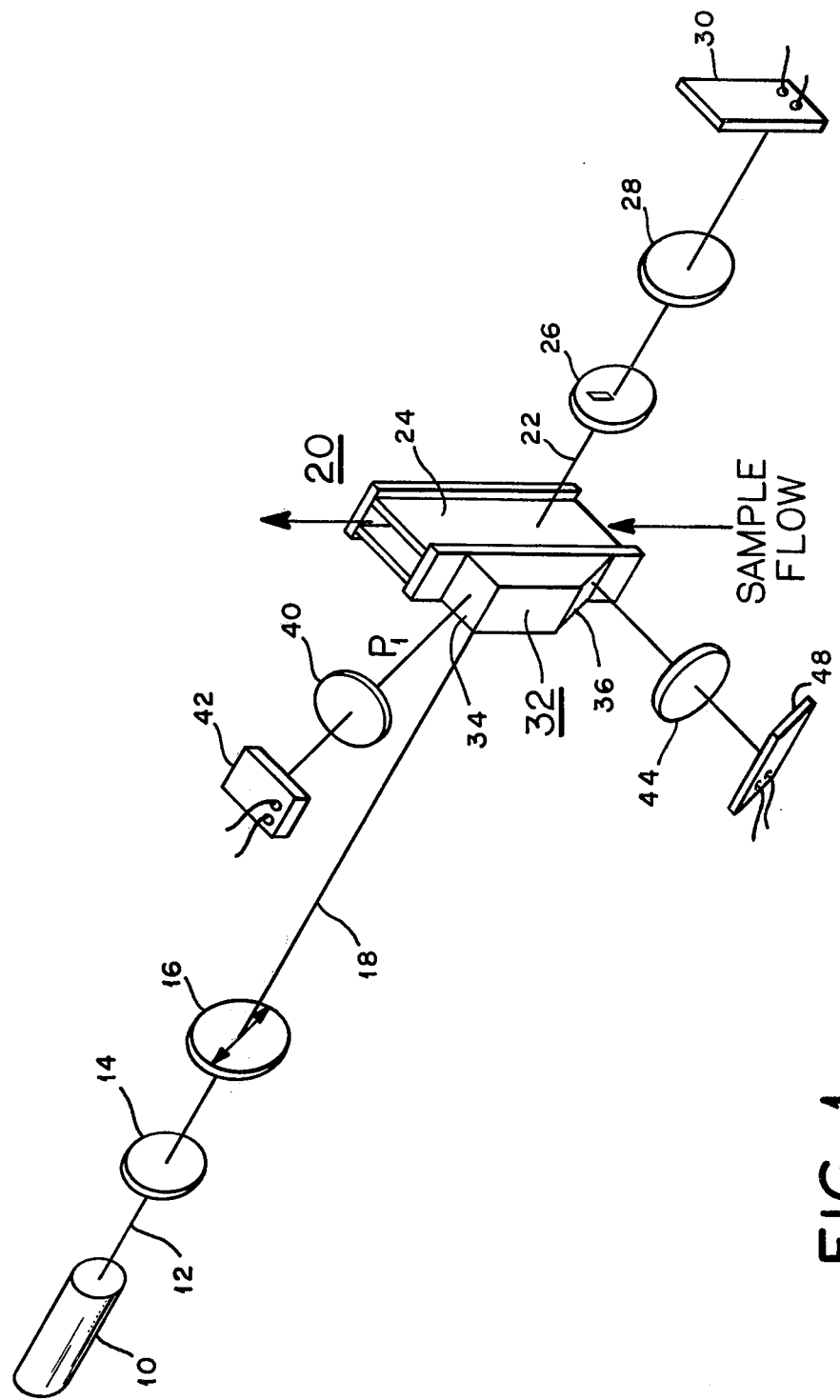
FIG. 1 is a drawing which shows the novel cell in an optical system in which it can be used.

An optical analyzing system of the type which requires the novel sample cell of this invention is shown in FIG. 1. A light source 10 produces a light beam 12 which is filtered through monochromatic filter 14 and polarized in the direction indicated by polarizer 16 to produce the beam 18 which is incident to the sample cell 20.

As indicated in FIG. 1 the sample cell 20 receives a continuous sample flow vertically through the cell cavity so that the liquid sample with its suspended particles intersects the path of beam 18. The scattered light which must be measured is that forward scattered in the direction of the beam axis and the light scattered at 90° to that axis and in two orthogonal directions, one of which is in the beam's plane of polarization.

As shown in FIG. 1 the incident beam 18 is received by the front of the cell which is an entrance window (not visible in FIG. 1). The forward scattered light 22 is transmitted through the back of the cell which forms an exit window 24. The forward scattered light then passes through a spatial filter 26 which is designed in accordance with the teaching of U.S. Pat. No. 3,873,206 so that the total light flux passed is a function of the volume of the suspended particles.

The filtered forward scattered light is focused by lens 28 onto photocell 30 which will produce an output proportional to the forward scattered light flux passed by filter 26. With an appropriate design of the aperture in filter 26, the output of photocell 30 can, for example, be proportional to the volume of the particles in the higher part of the size range being examined.

With the base of prism 32 optically contacting the sample along a side of cell 20, two of its faces 34 and 36 are positioned in angular relationship to the base such that the scattered light along axis $P_1$ is in the plane of polarization and that along $P_2$ is orthogonal to $P_1$.

The scattered light along axis $P_1$ is collected by lens 40 and focused on photocell 42 which then provides a signal proportional to the total flux along $P_1$. Similarly the scattered light along axis $P_2$ is focused by lens 44 onto photocell 48 which then provides a signal proportional to the scattered light along $P_2$.

As taught in U.S. Pat. No. 4,134,679, one can subtract the signal of photocell 42 from that of photocell 48 and obtain an indication of the total volume of those particles whose size is one-half of the wavelength passed by filter 14 or within a limited band around that size. The substitution of different monochromatic filters for filter 14 or the use of different light sources where 10 is a laser will extend the size range over which the volume distribution can be obtained. It will thus be evident from the arrangement of FIG. 1 that utilizing the signals from photocells 30, 42, and 48 one can determine the total volume of particles suspended in the flowing liquid sample or the size distribution.

Figure 2:
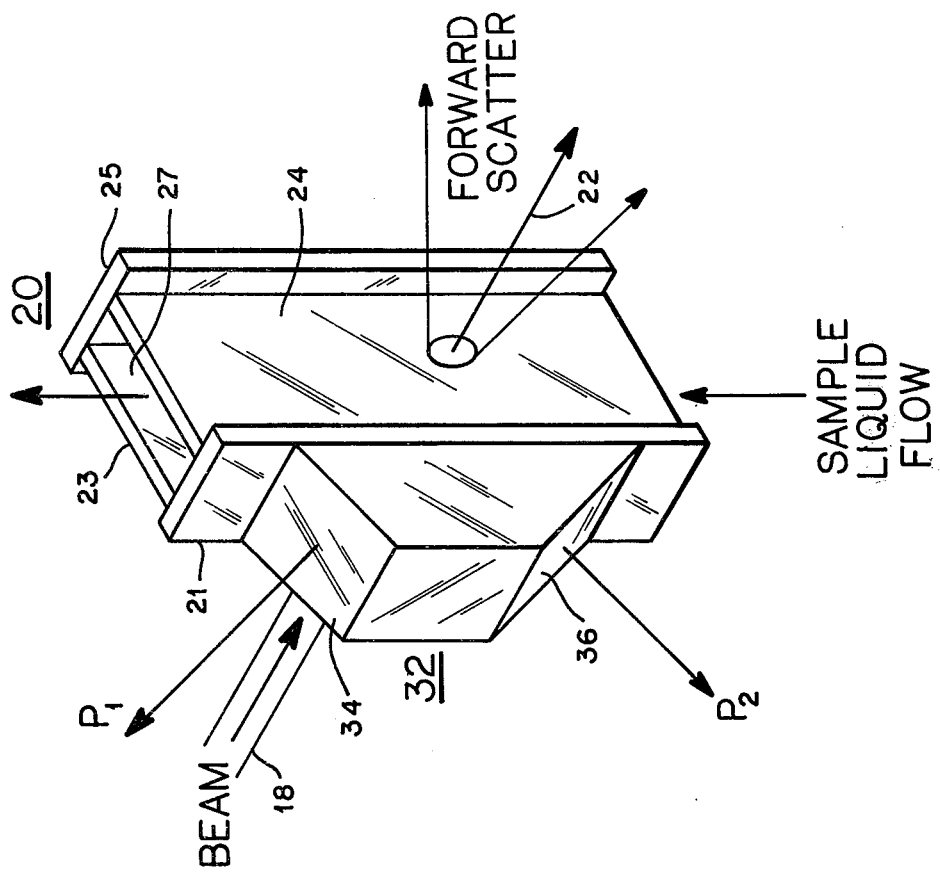
FIG. 2 is a perspective drawing of one form of the cell of FIG. 1.

FIG. 2 shows in perspective one form of the sample cell 20 of FIG. 1. In FIG. 2 the sample cell is constructed with 1×3 inch microscope slides 21, 23, 24, and 25 cemented together in parallel to form a chamber or cell cavity 27 with a rectangular cross-section through which the sample will flow. The chamber 27 is a straight walled chamber in that it is lacking in wells or insertions that would create turbulence.

The Dove prism 32 is optically cememted to the side 21 of the cell so that the faces 34 and 36 will be positioned to transmit along two orthogonal axis $P_1$ and $P_2$ the scattered light which appears at 90° from the beam axis. The faces 34 and 36 of the prism in FIG. 2 may, for example, be at 45° with the prism base shown cemented to side 21.

Figure 3:
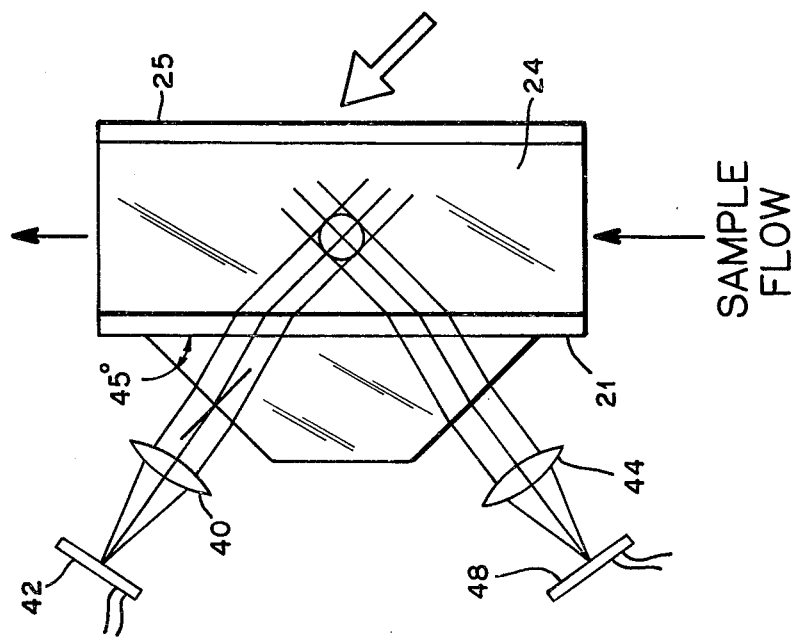
FIG. 3 is a back elevation of the cell of FIG. 2.

FIG. 3 shows a back elevation of the cell structure of FIG. 2 with the optical paths shown. The incident beam is linearly polarized in the plane indicated by the arrow. The relative positions of the photocells 42 and 48 with respect to the cell structure is such that they receive the scattered light at two orthogonal polarizations. The positioning will also depend upon the refractive index of the liquid sample.

For liquid suspensions a cell structure as is shown in FIGS. 2 and 3 but without the prism 32 would not be practical for the refraction that takes place at the interface between the glass side 21 and air would cause the light to emerge at a very steep angle, approaching total reflection. Proper alignment between the photocells and the sample chamber would be difficult to accomplish and polarization dependent reflection losses would be severe.

Figure 4:
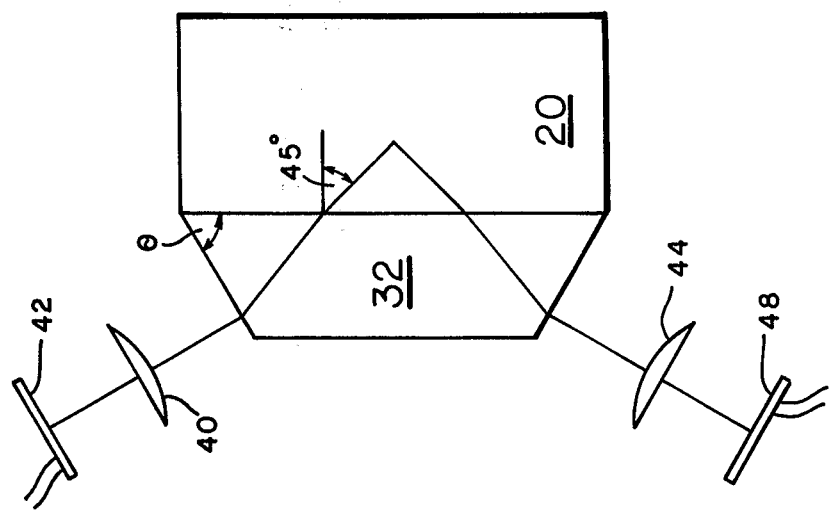
FIG. 4 is a schematic drawing showing the optical paths in a cell whose prism has a different angle than the prism of FIG. 2.

The prism angle of 45° shown in FIGS. 2 and 3 can be used because of the ready availability of 45° Dove prisms. Alternatively, the prism angle $\theta$ can be as shown in FIG. 4, namely one which allows the light ray to emerge normal to the prism face thus minimizing the difference between polarization dependent reflection losses. The angle $\theta$ can be calculated by the equation $$\sin \theta \frac{n_o}{n} \sin 45°$$

where n is the refractive index of the prism, and $n_o$ is the refractive index of the liquid in the cell. Thus, if $n_o=1.33$ as when water is the liquid and $n=1.51$ as when the prism is ordinary crown glass or BK-7, then $\theta=38.5°$.

Figure 5:
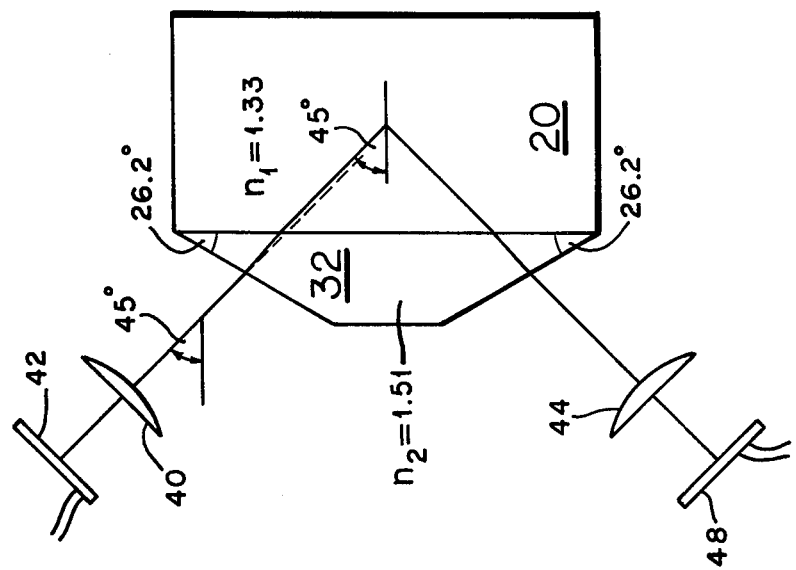
FIG. 5 is a drawing showing a prism with still another angle.

FIG. 5 shows the cell with a prism angle $\theta$ as 26.2° as would be required when $n_o=1.33$ and $n=1.51$, as assumed with regard to FIG. 4, if it is decided that the prism should refract the light so that the emerging beam makes an angle of 45° to the plane of the prism base. With such an arrangement the sample cell can be removed from its normal position without realignment of the photocells when aerosols or dry powders are involved.

The angle $\theta$ of FIG. 5 was calculated using the equation, $$\tan \theta = (n_o - 1)/\left(\sqrt{2n^2 - n_o^2} - 1\right)$$

and when
$n_o=1.330$
and $n=1.510$
then $\theta=26.198°$.

Figure 6:
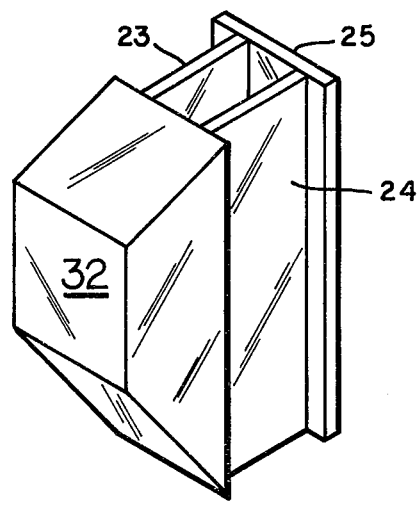
FIGS. 6, 7, and 8 show variations on the structure of FIG. 2.

In FIG. 6 there is shown an alternate type of construction. This structure differs from FIG. 2 in that the side 21 of the cell of FIG. 2 is omitted and the base of the prism 32 forms the inside wall of the cell.

Figure 7:
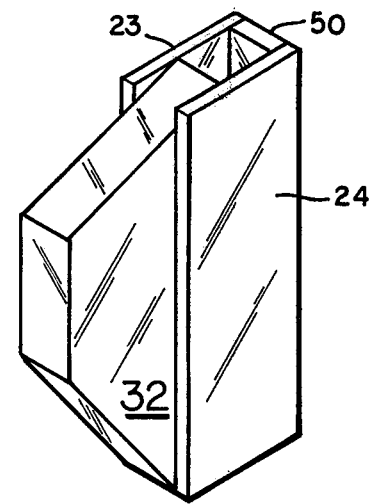

In FIG. 7 the prism 32 likewise forms the side of the cell as in FIG. 6 except the prism 32 is narrow in FIG. 7 so that it fits between the front and back and acts as a spacer. Also the front and back are separated by a spacer 50 which can be non-transmitting or diffusely transmitting.

Figure 8:
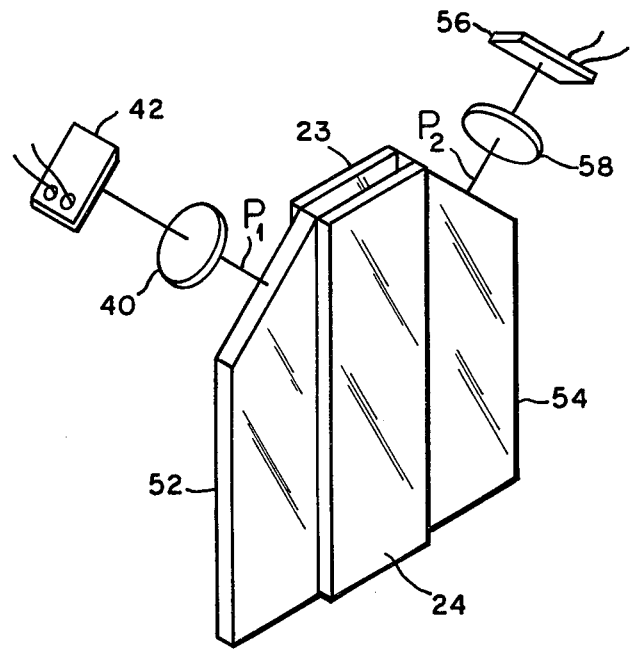

Still another arrangement for the cell can include two separate prisms such as shown in FIG. 8 where the prism 52 has one face for transmitting along axis $P_1$ to photocell 42 while the prism 54 also has one face for transmitting light along axis $P_2$ to photocell 56 by way of lens 58. Thus, in FIG. 8 the prism means is made up of two prisms each having a base which forms one interior wall of the cell. The advantage of this design is that only one angle and two faces are critical for each of the prisms used.

What is claimed is:

1. A straight path sample cell for the optical analysis of the light scattered by particles suspended in a flowing sample of liquid by measuring the components of light scattered in three mutually orthogonal directions from an incident light beam directed in one of those directions, and polarized in another, comprising:
   entrance and exit windows for said cell which are spaced to form a front and back for respectively receiving said light beam and transmitting as one of said orthogonal components the forward scattered light from the particles in said sample;
   prism means having at least one of its faces optically contacting said sample along a side of said cell and at least two other faces oriented so that said other faces each pass another of said orthogonal components of the scattered light, one of which is that component in the direction of polarization.

2. A sample cell as set forth in claim 1 in which the angle between the first face and each of said other faces is 45°.

3. A sample cell as set forth in claim 1 in which the angle between said one face and said other faces is such that the light rays travelling along the direction of the axis of the polarization exit the surface of said prism on a path normal to said surface.

4. A sample cell as set forth in claim 1 in which the angle between the first face and each of said other faces is such that the angle between the paths of the light leaving said other faces is 90°.

5. A sample cell as set forth in claim 1 in which the angle between said one face and said other faces is 38.5°.

6. A sample cell as set forth in claim 1 in which the angle between the first face and said other face is 26.2°.

7. A straight path sample cell for the optical analysis of the light scattered by particles suspended in a flowing sample of liquid by measuring the components of light scattered in three mutually orthogonal directions from an incident light beam directed in one of those directions and polarized in another, comprising:
   entrance and exit windows for said cell which are spaced to form a front and back for respectively receiving said light beam and transmitting as one of said orthogonal components the forward scattered light from the particles in said sample;
   a prism having one of its faces optically contacting said sample along a side of said cell and two other faces oriented at equal angles from said base so that said other faces each pass another of said orthogonal components of the scattered light, one of which is that component in the direction of polarization.

8. In a straight path sample cell having a flow path of rectangular cross section for the optical analysis of the light scattered by particles suspended in a sample of liquid flowing through said cell by measuring the components of light scattered in three mutually orthogonal directions from an incident light beam directed to produce forward scattered light in one of those directions and being polarized in another, the improvement which comprises:

prism means having at least one of its faces optically contacting said sample along a side of said cell and at least two other faces oriented so that said other faces each pass another of said orthogonal components of the scattered light, one of which is that component in the direction of polarization.

* * * * *